US010752563B2

(12) United States Patent
Yachi

(10) Patent No.: US 10,752,563 B2
(45) Date of Patent: Aug. 25, 2020

(54) HYDROGENATION METHOD

(71) Applicant: ZEON CORPORATION, Chiyoda-ku Tokyo (JP)

(72) Inventor: Yoshihide Yachi, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/084,714

(22) PCT Filed: Mar. 27, 2017

(86) PCT No.: PCT/JP2017/012425
§ 371 (c)(1),
(2) Date: Sep. 13, 2018

(87) PCT Pub. No.: WO2017/170421
PCT Pub. Date: Oct. 5, 2017

(65) Prior Publication Data
US 2019/0077729 A1 Mar. 14, 2019

(30) Foreign Application Priority Data

Mar. 31, 2016 (JP) ................. 2016-071367

(51) Int. Cl.
C07C 5/09 (2006.01)
B01J 23/44 (2006.01)
(Continued)

(52) U.S. Cl.
CPC ............... C07C 5/09 (2013.01); B01J 21/04 (2013.01); B01J 23/44 (2013.01); B01J 35/008 (2013.01);
(Continued)

(58) Field of Classification Search
None
See application file for complete search history.

(56) References Cited

U.S. PATENT DOCUMENTS 4,049,742 A   9/1977 Weitz et al.
4,230,897 A * 10/1980 Cosyns ................ B01J 23/44
                                            585/260
(Continued)

FOREIGN PATENT DOCUMENTS

CN   101434508 A   5/2009
CN   102285860 A   12/2011
(Continued)

OTHER PUBLICATIONS

Oct. 2, 2018, International Preliminary Report on Patentability issued in the International Patent Application No. PCT/JP2017/012425.
(Continued)

Primary Examiner — Ali Z Fadhel
(74) Attorney, Agent, or Firm — Kenja IP Law PC

(57) ABSTRACT

Provided is a hydrogenation method that with respect to a hydrocarbon mixture containing 1,3-butadiene and vinylacetylene, enables hydrogenation of vinylacetylene while inhibiting reduction of 1,3-butadiene concentration. The hydrogenation method is a method of hydrogenating a hydrocarbon mixture containing 1,3-butadiene and vinylacetylene that includes a step of bringing the hydrocarbon mixture and a hydrogenation catalyst into contact in the presence of hydrogen to hydrogenate at least vinylacetylene. The hydrocarbon mixture contains 1 mass % or more of vinylacetylene. The hydrogenation catalyst includes palladium and has a CO adsorption amount of 0.5 cm$^3$/g or less.

9 Claims, 1 Drawing Sheet

(51) Int. Cl.
  C07C 7/167 (2006.01)
  C07C 11/167 (2006.01)
  B01J 21/04 (2006.01)
  B01J 35/00 (2006.01)
  B01J 35/10 (2006.01)
  C07B 61/00 (2006.01)

(52) U.S. Cl.
  CPC ........... *B01J 35/1061* (2013.01); *C07C 7/167* (2013.01); *C07C 11/167* (2013.01); *C07B 61/00* (2013.01); *C07C 2523/44* (2013.01)

(56) References Cited

U.S. PATENT DOCUMENTS

| | | | |
|---|---|---|---|
| 4,440,956 | A | 4/1984 | Couvillion |
| 6,084,140 | A | 7/2000 | Kitamura et al. |
| 6,734,328 | B1 | 5/2004 | Ryu |
| 2003/0036669 | A1 | 2/2003 | Ryu et al. |
| 2006/0217579 | A1 | 9/2006 | Bailey |
| 2009/0030250 | A1* | 1/2009 | Hill .................... B01J 23/50 585/273 |
| 2010/0217052 | A1 | 8/2010 | Ungar et al. |
| 2010/0236986 | A1 | 9/2010 | Fischer et al. |
| 2012/0123174 | A1* | 5/2012 | Sugeta ................ B01J 23/002 585/273 |

FOREIGN PATENT DOCUMENTS

| | | |
|---|---|---|
| CN | 103787815 A | 5/2014 |
| JP | S51127006 A | 11/1976 |
| JP | S54135711 A | 10/1979 |
| JP | S5646824 A | 4/1981 |
| JP | S5653625 A | 5/1981 |
| JP | S5784745 A | 5/1982 |
| JP | S57123123 A | 7/1982 |
| JP | S5817835 A | 2/1983 |
| JP | S59162949 A | 9/1984 |
| JP | H04108540 A | 4/1992 |
| JP | 2004529759 A | 9/2004 |
| JP | 2006505613 A | 2/2006 |
| JP | 2006526499 A | 11/2006 |
| JP | 2010527776 A | 8/2010 |
| JP | 2011500327 A | 1/2011 |
| JP | 2011072913 A | 4/2011 |
| JP | 2011161426 A | 8/2011 |
| JP | 2013522018 A | 6/2013 |
| WO | 9810863 A1 | 3/1998 |
| WO | 2010035325 A1 | 4/2010 |
| WO | 2011113881 A2 | 9/2011 |

OTHER PUBLICATIONS

May 23, 2017, International Search Report issued in the International Patent Application No. PCT/JP2017/012425.

Oct. 4, 2019, the Extended European Search Report issued by the European Patent Office in the corresponding European Patent Application No. 17774958.7.

* cited by examiner

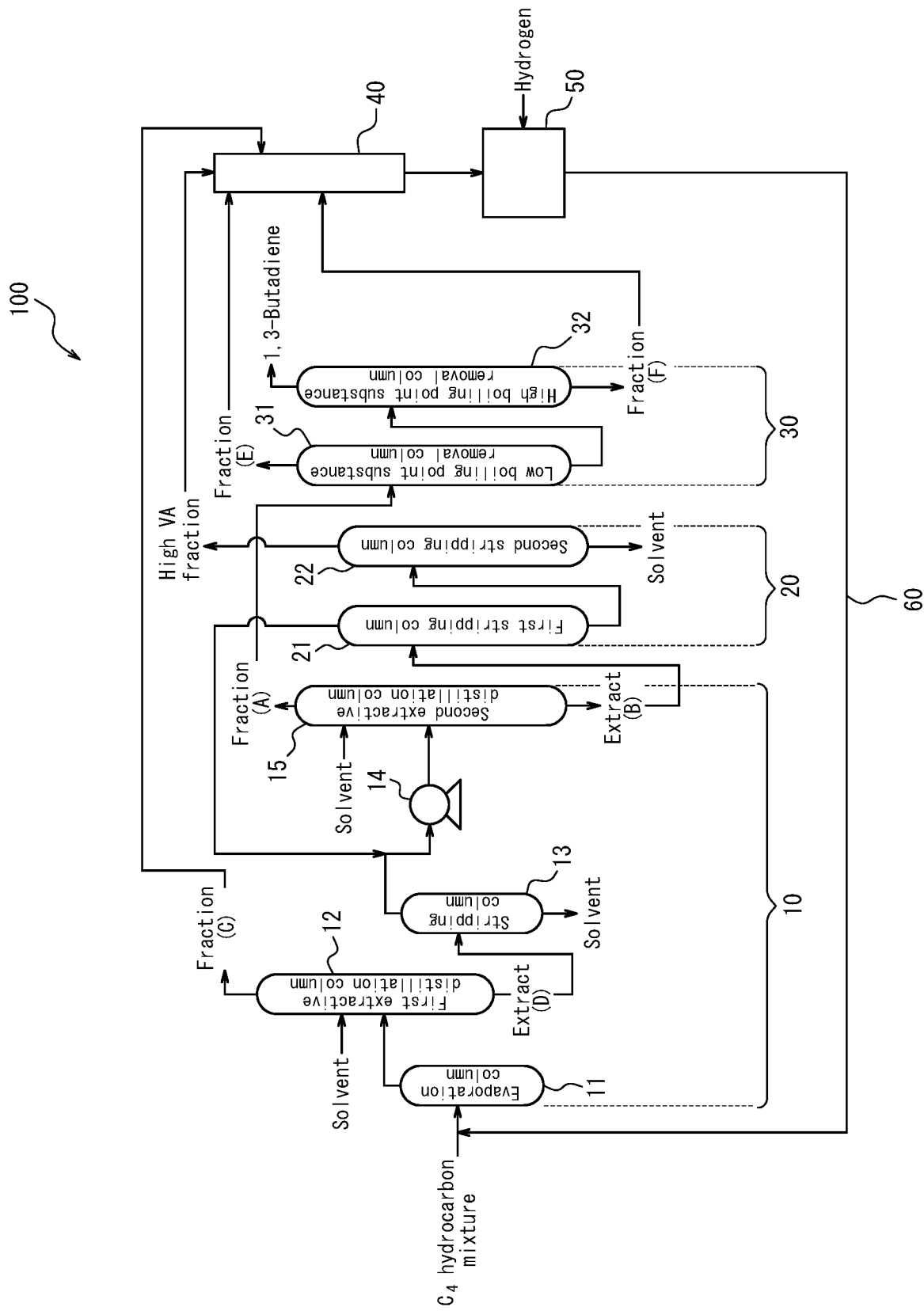

HYDROGENATION METHOD

TECHNICAL FIELD

The present disclosure relates to a hydrogenation method for a hydrocarbon mixture containing 1,3-butadiene and vinylacetylene.

BACKGROUND

There is demand for a technique for selectively hydrogenating vinylacetylene in a hydrocarbon mixture containing 1,3-butadiene and vinylacetylene, such as in a process of separating and recovering 1,3-butadiene in high purity from a $C_4$ hydrocarbon mixture such as a $C_4$ fraction. Specifically, there is demand for a technique that with respect to a hydrocarbon mixture containing 1,3-butadiene and vinylacetylene, enables selective hydrogenation of vinylacetylene while inhibiting hydrogenation of 1,3-butadiene, which is useful as a raw material for synthetic rubbers, resins, and the like.

In one example, PTL 1 proposes a technique for selectively hydrogenating vinylacetylene contained in a hydrocarbon mixture by using a palladium-promoted copper catalyst supported on alumina as a hydrogenation catalyst. In another example, PTL 2 proposes a technique for selectively hydrogenating vinylacetylene contained in a hydrocarbon mixture and reducing loss of 1,3-butadiene due to hydrogenation by using a palladium-based catalyst that includes at least one element selected from arsenic, selenium, antimony, and tellurium.

CITATION LIST

Patent Literature

PTL 1: JP 2006-505613 A
PTL 2: JP S56-46824 A

SUMMARY

Technical Problem

However, in hydrogenation of a hydrocarbon mixture containing 1,3-butadiene and vinylacetylene by a hydrogenation method using a conventional hydrogenation catalyst such as described above, it has not been possible to sufficiently inhibit hydrogenation of 1,3-butadiene and sufficiently inhibit reduction of 1,3-butadiene concentration in the resultant hydrogenated product.

Accordingly, an objective of the present disclosure is to provide a hydrogenation method that with respect to a hydrocarbon mixture containing 1,3-butadiene and vinylacetylene, enables hydrogenation of vinylacetylene while inhibiting reduction of 1,3-butadiene concentration.

Solution to Problem

The inventor conducted diligent investigation in order to achieve the objective set forth above. Through this investigation, the inventor discovered that when a hydrocarbon mixture containing 1,3-butadiene and vinylacetylene and having a vinylacetylene concentration of at least a specific value is subjected to hydrogenation treatment using a specific hydrogenation catalyst, vinylacetylene can be effectively hydrogenated while inhibiting reduction of 1,3-butadiene concentration, and in this manner completed the present disclosure.

Specifically, the present disclosure aims to advantageously solve the problems set forth above by disclosing a hydrogenation method for a hydrocarbon mixture containing 1,3-butadiene and vinylacetylene, comprising a step of bringing the hydrocarbon mixture and a hydrogenation catalyst into contact in the presence of hydrogen to hydrogenate at least the vinylacetylene, wherein the hydrocarbon mixture contains 1 mass % or more of vinylacetylene, and the hydrogenation catalyst includes palladium and has a CO adsorption amount of 0.5 $cm^3/g$ or less. When a hydrocarbon mixture containing 1 mass % or more of vinylacetylene is hydrogenated using a hydrogenation catalyst that includes palladium and has a CO adsorption amount of 0.5 $cm^3/g$ or less as set forth above, vinylacetylene can be hydrogenated while inhibiting reduction of 1,3-butadiene concentration.

The "CO adsorption amount" referred to in the present disclosure can be measured in accordance with a method described in the EXAMPLES section of the present specification.

In the presently disclosed hydrogenation method, the CO adsorption amount is preferably 0.05 $cm^3/g$ or less. When the CO adsorption amount of the hydrogenation catalyst is 0.05 $cm^3/g$ or less, vinylacetylene can be selectively hydrogenated to 1,3-butadiene while inhibiting excessive hydrogenation of the vinylacetylene. Consequently, it is possible to further inhibit reduction of 1,3-butadiene concentration in the resultant hydrogenated product, or even to increase the 1,3-butadiene concentration to a higher level than in the hydrocarbon mixture.

In the presently disclosed hydrogenation method, the hydrogenation catalyst preferably includes a support and palladium supported on the support. When a hydrogenation catalyst in which palladium is supported on a support is used, vinylacetylene can be efficiently hydrogenated while inhibiting reduction of 1,3-butadiene concentration.

Moreover, in the presently disclosed hydrogenation method, a supported amount of the palladium is preferably at least 0.1 mass % and not more than 5.0 mass %. When the supported amount of palladium is within the range set forth above, hydrogenation of vinylacetylene and inhibition of reduction of 1,3-butadiene concentration due to hydrogenation of 1,3-butadiene can both be effectively achieved.

The "supported amount of palladium" referred to in the present disclosure can be measured by X-ray fluorescence analysis.

Furthermore, in the presently disclosed hydrogenation method, the support preferably includes γ-alumina and at least one of α-alumina and θ-alumina. When a hydrogenation catalyst in which the support includes γ-alumina and at least one of α-alumina and θ-alumina is used, vinylacetylene can be selectively hydrogenated to 1,3-butadiene. Consequently, it is possible to further inhibit reduction of 1,3-butadiene concentration in the resultant hydrogenated product, or even to increase the 1,3-butadiene concentration to a higher level than in the hydrocarbon mixture.

Also, in the presently disclosed hydrogenation method, the hydrogenation catalyst preferably has an eggshell structure. When a hydrogenation catalyst having an eggshell structure is used, vinylacetylene can be efficiently hydrogenated while inhibiting reduction of 1,3-butadiene concentration.

Moreover, in the presently disclosed hydrogenation method, the hydrogenation catalyst preferably has an average pore diameter of at least 5.0 nm and not more than 30 nm. When the average pore diameter of the hydrogenation catalyst is within the range set forth above, hydrogenation of vinylacetylene and inhibition of reduction of 1,3-butadiene concentration due to hydrogenation of 1,3-butadiene can both be effectively achieved. The "average pore diameter" of a "hydrogenation catalyst" referred to in the present disclosure can be measured by a gas adsorption method.

Furthermore, in the step of the presently disclosed hydrogenation method, a gaseous state hydrocarbon mixture is preferably brought into contact with the hydrogenation catalyst. When a gaseous state hydrocarbon mixture is used, handling is easy, and polymerization of hydrocarbon compounds contained in the hydrocarbon mixture can be prevented.

Also, in the presently disclosed hydrogenation method, the hydrocarbon mixture preferably includes a fraction produced in separation and recovery of 1,3-butadiene from a $C_4$ hydrocarbon mixture. When hydrocarbon mixture that includes a fraction produced in separation and recovery of 1,3-butadiene from a $C_4$ hydrocarbon mixture is hydrogenated, 1,3-butadiene can be obtained in a high yield.

Advantageous Effect

According to the present disclosure, it is possible to hydrogenate vinylacetylene while inhibiting reduction of 1,3-butadiene concentration with respect to a hydrocarbon mixture containing 1,3-butadiene and vinylacetylene.

BRIEF DESCRIPTION OF THE DRAWING

In the accompanying drawing,
FIG. 1 illustrates schematic configuration of one example of a 1,3-butadiene production apparatus.

DETAILED DESCRIPTION

The following provides a detailed description of embodiments of the present disclosure.

A presently disclosed hydrogenation method can be used in hydrogenation of a hydrocarbon mixture containing 1,3-butadiene and vinylacetylene. Note that in a situation in which the concentration of 1,3-butadiene in a hydrogenated product obtained in the presently disclosed hydrogenation method is higher than the concentration of 1,3-butadiene in the pre-hydrogenation hydrocarbon mixture, the hydrogenation method can suitably be used in production of 1,3-butadiene from a hydrocarbon mixture.

(Hydrogenation Method)

The presently disclosed hydrogenation method includes a step of bringing a hydrocarbon mixture containing 1,3-butadiene and vinylacetylene and a hydrogenation catalyst into contact in the presence of hydrogen to hydrogenate at least vinylacetylene. Moreover, in the presently disclosed hydrogenation method, it is a requirement that a hydrocarbon mixture in which the concentration of vinylacetylene is at least a specific value is subjected to hydrogenation treatment using a specific hydrogenation catalyst.

As a result of a specific hydrocarbon mixture being subjected to hydrogenation treatment using a specific hydrogenation catalyst, the presently disclosed hydrogenation method enables hydrogenation of vinylacetylene while inhibiting reduction of 1,3-butadiene concentration in the resultant hydrogenated product due to hydrogenation of 1,3-butadiene.

<Hydrocarbon Mixture>

The hydrocarbon mixture that is hydrogenated by the presently disclosed hydrogenation method may be any hydrocarbon mixture that contains 1,3-butadiene and vinylacetylene, and in which the concentration of vinylacetylene is 1 mass % or more. More specifically, although no specific limitations are made, the hydrocarbon mixture is preferably a hydrocarbon mixture that includes a fraction produced in separation and recovery of 1,3-butadiene from a $C_4$ hydrocarbon mixture, such as a $C_4$ fraction obtained in production of ethylene through cracking of naphtha, and is more preferably a fraction produced in separation and recovery of 1,3-butadiene from a $C_4$ hydrocarbon mixture, or a mixture thereof. This is because when a hydrocarbon mixture that includes a fraction produced in separation and recovery of 1,3-butadiene from a $C_4$ hydrocarbon mixture is hydrogenated, 1,3-butadiene can be obtained in a high yield.

The fraction that is produced in separation and recovery of 1,3-butadiene from a $C_4$ hydrocarbon mixture is not specifically limited and examples thereof include:

(1) a fraction that is distilled in extractive distillation of a $C_4$ hydrocarbon mixture using a solvent and that contains hydrocarbons (for example, butanes and butenes) having lower solubility than butadiene (1,2-butadiene and 1,3-butadiene) with respect to the solvent;

(2) a fraction produced when a fraction containing butadiene in high concentration that is obtained through extractive distillation of a $C_4$ hydrocarbon mixture is purified to obtain 1,3-butadiene; and (3) a fraction produced when solvent is recovered from an extract (bottom liquid) containing acetylene that is drained from the bottom in extractive distillation of a $C_4$ hydrocarbon mixture using the solvent.

[Vinylacetylene Concentration]

The concentration of vinylacetylene in the hydrocarbon mixture is required to be 1 mass % or more. In a situation in which the concentration of vinylacetylene is less than 1 mass %, it is not possible to inhibit hydrogenation of 1,3-butadiene in the hydrocarbon mixture, and 1,3-butadiene concentration in the resultant hydrogenated product is reduced even if a specific hydrogenation catalyst is used.

Note that the concentration of vinylacetylene in the hydrocarbon mixture is preferably 20 mass % or less, and more preferably 15 mass % or less from a viewpoint of preventing abnormal reactions because vinylacetylene is highly reactive and readily undergoes abnormal reactions. On the other hand, the concentration of vinylacetylene in the hydrocarbon mixture is preferably 5 mass % or more, and more preferably 10 mass % or more from a viewpoint of sufficiently inhibiting hydrogenation of 1,3-butadiene.

[1,3-Butadiene Concentration]

The concentration of 1,3-butadiene in the hydrocarbon mixture is preferably 5 mass % or more, and more preferably 10 mass % or more, and is preferably 25 mass % or less, and more preferably 20 mass % or less. When the concentration of 1,3-butadiene in the hydrocarbon mixture is at least any of the lower limits set forth above, the 1,3-butadiene concentration in a hydrogenated product obtained through hydrogenation of the hydrocarbon mixture can be appropriately increased, and thus recovery efficiency of 1,3-butadiene from the hydrogenated product can be increased. Moreover, when the concentration of 1,3-butadiene in the hydrocarbon mixture is not more than any of the upper limits set forth above, hydrogenation of 1,3-butadiene can be inhibited, and reduction of 1,3-butadiene concentration in the resultant hydrogenated product can be sufficiently inhibited.

<Hydrogenation Catalyst>

The hydrogenation catalyst used in the presently disclosed hydrogenation method is required to include palladium and have a CO adsorption amount of 0.5 cm$^3$/g or less. In a situation in which the hydrogenation catalyst does not include palladium and/or has a CO adsorption amount of more than 0.5 cm$^3$/g, it is not possible to inhibit hydrogenation of 1,3-butadiene in the hydrocarbon mixture, and the 1,3-butadiene concentration in the resultant hydrogenated product is reduced even if the concentration of vinylacetylene in the hydrocarbon mixture is 1 mass % or more.

[Active Component]

Although the hydrogenation catalyst may include elements other than palladium (for example, copper, nickel, and platinum), it is preferable that the hydrogenation catalyst is a single-component catalyst that only includes palladium as an active component.

The active component of the hydrogenation catalyst may be used in hydrogenation of the hydrocarbon mixture in a supported state on a support but is not specifically limited to being used in this manner. In other words, the hydrogenation catalyst used in the presently disclosed hydrogenation method is preferably a catalyst in which an active component including palladium is supported on a support, and is more preferably a catalyst in which only palladium is supported on a support.

[Support]

The support of the hydrogenation catalyst is not specifically limited and may be a support made of a known support material such as a zeolite or alumina. Of such supports, a support that includes γ-alumina and at least one of α-alumina and θ-alumina is preferable. This is because when a hydrogenation catalyst that includes a support including γ-alumina and at least one of α-alumina and θ-alumina is used, vinylacetylene in the hydrocarbon mixture can be selectively hydrogenated to 1,3-butadiene, and it is possible to further inhibit reduction of 1,3-butadiene concentration in the resultant hydrogenated product, or even to increase the 1,3-butadiene concentration to a higher level than in the hydrocarbon mixture.

The hydrogenation catalyst that includes a support including γ-alumina and at least one of α-alumina and θ-alumina can be obtained by mounting an active component on a support including γ-alumina, and subsequently baking the active component and the support at 1000° C. or higher, for example, but is not specifically limited to being obtained in this manner.

[Supported Amount]

In a case in which the active component is supported on a support, the supported amount of palladium in the hydrogenation catalyst is preferably 0.1 mass % or more, and more preferably 0.2 mass % or more, and is preferably 5.0 mass % or less, and more preferably 1.0 mass % or less. When the supported amount of palladium is at least any of the lower limits set forth above, vinylacetylene can be effectively hydrogenated. Moreover, when the supported amount of palladium is not more than any of the upper limits set forth above, reduction of 1,3-butadiene concentration due to hydrogenation of 1,3-butadiene can be sufficiently inhibited.

[Structure]

Although no specific limitations are placed on the structure of the hydrogenation catalyst, it is preferable that the hydrogenation catalyst has an eggshell structure in a case in which the active component is supported on a support. When a hydrogenation catalyst having an eggshell structure is used, vinylacetylene can be efficiently hydrogenated while inhibiting reduction of 1,3-butadiene concentration.

The hydrogenation catalyst having an eggshell structure can be produced by a known technique without any specific limitations.

In the case of a hydrogenation catalyst having an eggshell structure, the thickness of a layer of active component including palladium is not specifically limited but may, for example, be at least 0.05 mm and not more than 2.0 mm. The thickness of the active component layer can be adjusted by a known technique. Moreover, the thickness of the active component layer can be measured by scanning electron microscope energy dispersive X-ray spectroscopy (SEM-EDX).

[Properties]

The hydrogenation catalyst used in the presently disclosed hydrogenation method is required to have a CO adsorption amount of 0.5 cm$^3$/g or less, and preferably also has the properties described below.

[[CO Adsorption Amount]]

The CO adsorption amount of the hydrogenation catalyst is preferably 0.1 cm$^3$/g or less, more preferably 0.05 cm$^3$/g or less, and even more preferably 0.045 cm$^3$/g or less, and is preferably 0.001 cm$^3$/g or more, and more preferably 0.005 cm$^3$/g or more. This is because when the CO adsorption amount is within any of the ranges set forth above, vinylacetylene in the hydrocarbon mixture can be selectively hydrogenated to 1,3-butadiene while inhibiting excessive hydrogenation of the vinylacetylene, and it is possible to further inhibit reduction of 1,3-butadiene concentration in the resultant hydrogenated product, or even to increase the 1,3-butadiene concentration to a higher level than in the hydrocarbon mixture.

[[Average Pore Diameter]] The average pore diameter of the hydrogenation catalyst is preferably 5.0 nm or more, more preferably 10 nm or more, and even more preferably 15 nm or more, and is preferably 30 nm or less, and more preferably 25 nm or less. When the average pore diameter of the hydrogenation catalyst is within any of the ranges set forth above, hydrogenation of vinylacetylene and inhibition of reduction of 1,3-butadiene concentration due to hydrogenation of 1,3-butadiene can both be effectively achieved.

[[Specific Surface Area]]

The specific surface area of the hydrogenation catalyst is preferably 10 m$^2$/g or more, and more preferably 20 m$^2$/g or more, and is preferably 200 m$^2$/g or less, and more preferably 100 m$^2$/g or less. When the specific surface area of the hydrogenation catalyst is within any of the ranges set forth above, hydrogenation of vinylacetylene and inhibition of reduction of 1,3-butadiene concentration due to hydrogenation of 1,3-butadiene can both be effectively achieved.

The term "specific surface area" as used in the present disclosure refers to BET specific surface area measured by a gas adsorption method.

The properties of the hydrogenation catalyst set forth above (for example, CO adsorption amount, average pore diameter, and specific surface area) can be adjusted by altering the production conditions of the hydrogenation catalyst. In one specific example, the CO adsorption amount and specific surface area decrease, and the average pore diameter increases when a catalyst in which an active component is supported on a support is subjected to baking treatment.

[Production Method of Hydrogenation Catalyst]

The hydrogenation catalyst set forth above can be produced by optionally mounting an active component including palladium on a support by a known technique, and then optionally performing baking of the active component and the support supporting the active component in an oxygencontaining atmosphere, such as air, or an inert gas atmosphere, such as nitrogen, for example, but is not specifically limited to being produced in this manner. In particular, from a viewpoint of obtaining a hydrogenation catalyst that can further inhibit reduction of 1,3-butadiene concentration due to hydrogenation of 1,3-butadiene, the hydrogenation catalyst is preferably produced through baking of an active component and a support supporting the active component, and is more preferably produced through baking of an active component and a support supporting the active component at a temperature of 1000° C. or higher. The baking time is not specifically limited but is preferably 1 hour or more, and more preferably at least 2 hours and not more than 10 hours.

<Hydrogenation>

In the presently disclosed hydrogenation method, hydrogenation of vinylacetylene contained in the hydrocarbon mixture set forth above is performed by bringing the hydrocarbon mixture and the hydrogenation catalyst set forth above into contact in the presence of hydrogen. The hydrogenation may be performed by a batch process, a semi-batch process, or a continuous process.

[Hydrogenation Conditions]

The supplied amount and supplied pressure of hydrogen are not specifically limited and may be set as a supplied amount and a supplied pressure that enable sufficient hydrogenation of vinylacetylene contained in the hydrocarbon mixture. Specifically, the supplied amount of hydrogen may, for example, be set such as to have a volume ratio relative to the hydrocarbon mixture of at least 0.2 and not more than 2.0. Moreover, the supplied pressure (gauge pressure) of hydrogen may, for example, be set as at least 0 kPa and not more than 300 kPa.

Also note that the hydrogen may be supplied in the form of a mixed gas with an inert gas such as nitrogen. In the case of a mixed gas, the ratio of inert gas is, for example, set as a volume ratio relative to hydrogen of at least 0.1 and not more than 2.0. Moreover, the supplied pressure (gauge pressure) of the mixed gas may, for example, be set as at least 0 kPa and not more than 300 kPa.

The hydrocarbon mixture that is brought into contact with the hydrogenation catalyst may be brought into contact with the hydrogenation catalyst in a liquid state or may be brought into contact with the hydrogenation catalyst in a gaseous state. Of the above, a case in which the hydrocarbon mixture is brought into contact with the hydrogenation catalyst in a gaseous state is preferable (i.e., a case in which hydrogenation is carried out as a gas phase reaction is preferable) from a viewpoint of ease of handling and prevention of polymerization of hydrocarbon compounds contained in the hydrocarbon mixture.

The supplied pressure (gauge pressure) of the hydrocarbon mixture may, for example, be set as at least 0 kPa and not more than 300 kPa.

The temperature at which the hydrocarbon mixture and the hydrogenation catalyst are brought into contact is not specifically limited and may be any temperature at which vinylacetylene contained in the hydrocarbon mixture can be hydrogenated. Specifically, the temperature at which the hydrocarbon mixture and the hydrogenation catalyst are brought into contact may, for example, be at least 10° C. and not higher than 50° C.

[Properties of Hydrogenated Product]

The concentration of vinylacetylene in the hydrogenated product obtained through hydrogenation of the hydrocarbon mixture is preferably less than 5 mass %, more preferably 3 mass % or less, and even more preferably 1 mass % or less. When the concentration of vinylacetylene is not more than any of the upper limits set forth above, abnormal reaction of the hydrogenated product can be inhibited.

The concentration of 1,3-butadiene in the hydrogenated product ($C_A$; units: mass %) is preferably a concentration such that a difference ($C_A-C_B$) with the concentration of 1,3-butadiene in the hydrocarbon mixture ($C_B$; units: mass %) has a value of −3.0 mass % or higher (i.e., $C_A \geq C_B-3.0$), is more preferably at least the concentration of 1,3-butadiene in the hydrocarbon mixture (i.e., $C_A \geq C_B$), and is even more preferably higher than the concentration of 1,3-butadiene in the hydrocarbon mixture (i.e., $C_A > C_B$). When the difference in 1,3-butadiene concentration ($C_A-C_B$) has a value of −3.0 mass % or higher, hydrogenation of 1,3-butadiene can be sufficiently inhibited. Note that in a case in which the concentration of 1,3-butadiene in the hydrogenated product becomes higher than the concentration of 1,3-butadiene in the hydrocarbon mixture (i.e., when the amount of vinylacetylene that is selectively hydrogenated to 1,3-butadiene is larger than the amount of 1,3-butadiene that is hydrogenated), 1,3-butadiene can be efficiently produced using the presently disclosed hydrogenation method.

The concentration of 1,3-butadiene in the hydrogenated product is preferably 10 mass % or more, and more preferably 15 mass % or more. This is because 1,3-butadiene can be efficiently separated and recovered from the hydrogenated product when the concentration of 1,3-butadiene is at least any of the lower limits set forth above. The concentration of 1,3-butadiene in the hydrogenated product is normally 40 mass % or less.

1,3-Butadiene in the resultant hydrogenated product may, without any specific limitations, be recovered by a known separation and recovery method and be used as a raw material for a synthetic rubber, resin, or the like.

<Example of Application of Hydrogenation Method>

The presently disclosed hydrogenation method set forth above is particularly suitable for use in hydrogenation of a fraction produced as a by-product in a process of separating and recovering 1,3-butadiene from a $C_4$ hydrocarbon mixture by extractive distillation but is not specifically limited to being used in this manner.

More specifically, the presently disclosed hydrogenation method can suitably be used in a 1,3-butadiene production apparatus 100 such as illustrated in FIG. 1 for when a fraction produced as a by-product in separation and recovery of 1,3-butadiene from a $C_4$ hydrogenation method by extractive distillation is hydrogenated in a hydrogenation section 50.

The production apparatus 100 illustrated in FIG. 1 includes an extractive distillation section 10 in which a fraction (A) containing 1,3-butadiene and an extract (B) containing vinylacetylene are obtained through extractive distillation of a $C_4$ hydrocarbon mixture such as a $C_4$ fraction, a stripping section 20 in which a high VA fraction containing vinylacetylene is obtained by removing solvent from the extract (B) obtained in the extractive distillation section 10, and an impurity removal section 30 in which impurities other than 1,3-butadiene are removed from the fraction (A) obtained in the extractive distillation section 10.

The production apparatus 100 also includes a mixing section 40 in which the high VA fraction obtained in the stripping section 20 is mixed with at least one and preferably both of a fraction produced in the extractive distillation section 10 and a fraction produced in the impurity removal section 30 to obtain a diluted fraction in which the concentration of vinylacetylene is lower than in the high VA fraction, a hydrogenation section 50 in which the diluted fraction obtained in the mixing section 40 is subjected to hydrogenation treatment by the presently disclosed hydrogenation method to hydrogenate vinylacetylene in the diluted fraction, and an optional return line 60 by which a hydrogenated product obtained in the hydrogenation section 50 is returned to the extractive distillation section 10.

The extractive distillation section 10 includes, for example, an evaporation column 11 in which the $C_4$ hydrocarbon mixture is vaporized, a first extractive distillation column 12 in which the $C_4$ hydrocarbon mixture vaporized in the evaporation column 11 is separated into a fraction (C) and an extract (D) by extractive distillation, a stripping column 13 in which solvent is removed from the extract (D), a compressor 14 in which a fraction obtained through removal of solvent from the extract (D) is pressurized, and a second extractive distillation column 15 in which the fraction pressurized by the compressor 14 is separated into a fraction (A) and an extract (B) by extractive distillation.

In the first extractive distillation column 12, by supplying solvent from an upper level relative to a supply level of the $C_4$ hydrocarbon mixture and performing extractive distillation of the $C_4$ hydrocarbon mixture, a fraction (C) containing butanes, butenes, and the like that have lower solubility than 1,3-butadiene with respect to the solvent is distilled from the top of the column and an extract (D) containing 1,3-butadiene and vinylacetylene is drained from the bottom of the column.

Moreover, in the stripping column 13, solvent is drained from the bottom of the column and a fraction containing 1,3-butadiene and vinylacetylene is distilled from the top of the column. Note that solvent that is recovered in the stripping column 13 may optionally be reused in the first extractive distillation column 12, the second extractive distillation column 15, or the like.

In the second extractive distillation column 15, by supplying solvent from an upper level relative to a supply level of the fraction containing 1,3-butadiene and vinylacetylene that is distilled from the stripping column 13 and performing extractive distillation of the fraction containing 1,3-butadiene and vinylacetylene, a fraction (A) containing 1,3-butadiene is distilled from the top of the column and an extract (B) containing vinylacetylene and the like that have higher solubility than 1,3-butadiene with respect to the solvent is drained from the bottom of the column.

The stripping section 20 includes, for example, a first stripping column 21 for recovering 1,3-butadiene that is mixed into the extract (B) and a second stripping column 22 in which solvent is removed from the extract (B), after recovery of 1,3-butadiene therefrom, to obtain a high VA fraction containing vinylacetylene.

In the first stripping column 21, a fraction containing 1,3-butadiene that was mixed into the extract (B) is distilled from the top of the column and a bottom liquid containing vinylacetylene is drained from the bottom of the column. The fraction containing 1,3-butadiene that is distilled from the top of the first stripping column 21 may optionally be returned to the second extractive distillation column 15.

In the second stripping column 22, a high VA fraction containing vinylacetylene that was contained in the bottom liquid from the first stripping column 21 is distilled from the top of the column and solvent is drained from the bottom of the column. Note that solvent that is recovered in the second stripping column 22 may optionally be reused in the first extractive distillation column 12, the second extractive distillation column 15, or the like.

The impurity removal section 30 includes, for example, a low boiling point substance removal column 31 in which impurities having a lower boiling point than 1,3-butadiene that are contained in the fraction (A) obtained in the second extractive distillation column 15 are removed and a high boiling point substance removal column 32 in which impurities having a higher boiling point than 1,3-butadiene are removed.

In the low boiling point substance removal column 31, a fraction (E) containing low boiling point impurities such as methylacetylene is distilled from the top of the column and a bottom liquid in which 1,3-butadiene is enriched is drained from the bottom of the column.

In the high boiling point substance removal column 32, a fraction in which 1,3-butadiene is further enriched is distilled from the top of the column and a fraction (F) containing high boiling point impurities such as 1,2-butadiene is drained from the bottom of the column.

In the mixing section 40, at least one selected from the group consisting of the fraction (C) produced in the first extractive distillation column 12, the fraction (E) produced in the low boiling point substance removal column 31, and the fraction (F) produced in the high boiling point substance removal column 32 is mixed with the high VA fraction obtained in the stripping section 20 to obtain a diluted fraction. Since the concentrations of vinylacetylene in the fractions (C), (E), and (F) are lower than the concentration of vinylacetylene in the high VA fraction, the concentration of vinylacetylene in the diluted fraction is also lower than the concentration of vinylacetylene in the high VA fraction. Consequently, abnormal reactions of the high VA fraction can be prevented in the production apparatus 100.

No specific limitations are placed on the mixing section 40 so long as the high VA fraction and at least one selected from the group consisting of the fractions (C), (E), and (F) can be homogeneously mixed. For example, the mixing section 40 may be a mixing device such as an inline mixer or may be a junction pipe.

In the mixing section 40, the high VA fraction is diluted such that the resultant diluted fraction (hydrocarbon mixture) contains 1,3-butadiene and the concentration of vinylacetylene in the diluted fraction is 1 mass % or more.

In the hydrogenation section 50, the diluted fraction obtained in the mixing section 40 is subjected to hydrogenation treatment to hydrogenate vinylacetylene in the diluted fraction.

The hydrogenation section 50 is not specifically limited and may, for example, be a hydrogenation apparatus that includes a reactor having the hydrogenation catalyst set forth above loaded therein and a hydrogen supply line for supplying hydrogen into the reactor, and optionally further includes an evaporator for vaporizing the diluted fraction that is supplied into the reactor.

The return line 60 connects the hydrogenation section 50 and the extractive distillation section 10, and returns a hydrogenated product obtained in the hydrogenation section 50 to the extractive distillation section 10. Specifically, the return line 60 connects an outlet of the hydrogenation section 50 and the evaporation column 11 of the extractive distillation section 10. The hydrogenated product that is returned via the return line 60 is mixed with the $C_4$ hydrocarbon mixture and is supplied to the extractive distillation section 10. Consequently, 1,3-butadiene that is contained in the hydrogenated product can be efficiently separated and recovered together with 1,3-butadiene that is contained in the $C_4$ hydrocarbon mixture.

A condenser or a pressurized blower for condensing the hydrogenated product may be included in the return line 60.

As a result of the presently disclosed hydrogenation method being adopted in the production apparatus 100, the production apparatus 100 enables efficient production of 1,3-butadiene.

EXAMPLES

The following provides a more detailed description of the present disclosure through examples. However, the present disclosure is not limited to these examples.

In the examples and comparative examples, the CO adsorption amount and specific surface area of a hydrogenation catalyst, the composition of a hydrocarbon mixture, and the composition of a hydrogenated product were measured by the following methods.

<CO Adsorption Amount>

A metal dispersion measurement device (BEL-METAL III produced by MicrotracBEL Corp.) was used to measure the adsorbed amount of carbon monoxide (CO) at 50° C. by a CO pulse adsorption method with respect to a measurement sample that had been reduced at 200° C. using hydrogen.

<Specific Surface Area>

Specific surface area was measured using a specific surface area analyzer (FlowSorb II produced by Shimadzu Corporation). Specifically, a measurement sample was cooled by liquid nitrogen and adsorption of $N_2$ was carried out in a mixed gas atmosphere of $N_2$/He in a 30/70 volume ratio, and then the amount of desorbed $N_2$ when the measurement sample was returned to room temperature was quantified, and the specific surface area was determined from the desorbed amount of $N_2$ by the BET method.

<Composition>

The compositions of a hydrocarbon mixture and a hydrogenated product were measured using a gas chromatograph (7890A produced by Agilent Technologies) under the following conditions.

Gas chromatograph: Agilent® 7890A (Agilent is a registered trademark in Japan, other countries, or both) produced by Agilent Technologies Column: Agilent 19091P-S33, 30.0 m×250 μm×5.00 μm Column temperature: 35° C.×2.5 min⇒heated at 5° C./min⇒100° C.⇒heated at 10° C./min⇒180° C.×10 min Injection temperature: 200° C.

Detector temperature: 200° C.

Carrier gas: Helium

Split ratio: 200/1

Detector: FID

Example 1

<Production of Hydrogenation Catalyst>

A commercially available catalyst that included palladium supported on a γ-alumina support and had an eggshell structure (produced by JGC Catalysts and Chemicals Ltd.; product name: N1182AZ; supported amount of palladium: 0.5 mass %; CO adsorption amount: 0.3456 cm³/g; specific surface area: 159 m²/g; average pore diameter: 10.4 nm) was baked for 3 hours at 1000° C. in an air atmosphere to produce a hydrogenation catalyst. The CO adsorption amount and specific surface area of the hydrogenation catalyst were measured. The results are shown in Table 2.

When the support of the obtained hydrogenation catalyst was analyzed by X-ray diffraction analysis, peaks attributed to γ-alumina and peaks attributed to α-alumina and θ-alumina were observed. Moreover, the obtained hydrogenation catalyst had an eggshell structure. Furthermore, the average pore diameter of the obtained hydrogenation catalyst was 19.3 nm.

The average pore diameter of the catalyst was determined by measuring the amount of adsorption with nitrogen with respect to catalyst that had been dried for 120 minutes at 130° C. under reduced pressure using a volumetric gas adsorption analyzer (BELSORP-mini II).

<Hydrogenation of Hydrocarbon Mixture>

A hydrocarbon mixture A having a composition shown in Table 1 was produced by mixing fractions produced as by-products in separation and recovery of 1,3-butadiene by extractive distillation from a $C_4$ fraction obtained in cracking of naphtha to produce ethylene.

A jacketed reactor (capacity: 0.02 L) in which the hydrogenation catalyst was loaded was prepared. The produced hydrogenation catalyst was loaded into the reactor.

Next, vaporized hydrocarbon mixture (flow rate: 50 mL/min; pressure (gauge pressure): 5 kPa) and hydrogen gas (flow rate: 25 mL/min; pressure (gauge pressure): 5 kPa) were continuously supplied into the reactor, and the hydrocarbon mixture A was hydrogenated at 25° C. The composition of the resultant hydrogenated product was measured. The results are shown in Table 2.

Example 2

A hydrogenation catalyst was produced and a hydrocarbon mixture was hydrogenated in the same way as in Example 1 with the exception that the temperature at which baking of the commercially available catalyst was performed in production of the hydrogenation catalyst was changed to 1100° C. Measurements were performed in the same way as in Example 1. The results are shown in Table 2.

When the support of the obtained hydrogenation catalyst was analyzed by X-ray diffraction analysis, peaks attributed to γ-alumina and peaks attributed to α-alumina and θ-alumina were observed. Moreover, the obtained hydrogenation catalyst had an eggshell structure.

Example 3

A hydrogenation catalyst was produced and a hydrocarbon mixture was hydrogenated in the same way as in Example 1 with the exception that the temperature at which baking of the commercially available catalyst was performed in production of the hydrogenation catalyst was changed to 900° C. Measurements were performed in the same way as in Example 1. The results are shown in Table 2.

Note that the obtained hydrogenation catalyst had an eggshell structure.

Example 4

Hydrogenation of a hydrocarbon mixture was performed in the same way as in Example 1 with that exception that the commercially available catalyst was used as a hydrogenation catalyst without performing baking. Measurements were performed in the same way as in Example 1. The results are shown in Table 2.

Comparative Example 1

A hydrogenation catalyst was produced and a hydrocarbon mixture was hydrogenated in the same way as in Example 1 with the exception that a hydrocarbon mixture B composed of a $C_4$ fraction having a composition shown in Table 1 was used instead of the hydrocarbon mixture A. Measurements were performed in the same way as in Example 1. The results are shown in Table 2.

Comparative Example 2

A hydrogenation catalyst was produced and a hydrocarbon mixture was hydrogenated in the same way as in Example 2 with the exception that a hydrocarbon mixture B composed of a $C_4$ fraction having a composition shown in Table 1 was used instead of the hydrocarbon mixture A. Measurements were performed in the same way as in Example 1. The results are shown in Table 2.

Comparative Example 3

A hydrogenation catalyst was produced and a hydrocarbon mixture was hydrogenated in the same way as in Example 3 with the exception that a hydrocarbon mixture B composed of a $C_4$ fraction having a composition shown in Table 1 was used instead of the hydrocarbon mixture A. Measurements were performed in the same way as in Example 1. The results are shown in Table 2.

Comparative Example 4

A hydrogenation catalyst was produced and a hydrocarbon mixture was hydrogenated in the same way as in Example 4 with the exception that a hydrocarbon mixture B composed of a $C_4$ fraction having a composition shown in Table 1 was used instead of the hydrocarbon mixture A. Measurements were performed in the same way as in Example 1. The results are shown in Table 2.

TABLE 1

|  | Hydrocarbon mixture A | Hydrocarbon mixture B |
|---|---|---|
| i-Butane [mass %] | 2.78 | 3.42 |
| n-Butane [mass %] | 2.91 | 6.49 |
| trans-2-Butene [mass %] | 3.24 | 4.28 |
| 1-Butene [mass %] | 7.42 | 12.44 |
| iso-Butene [mass %] | 16.56 | 27.07 |
| cis-2-Butene [mass %] | 30.48 | 3.36 |
| 1,2-Butadiene [mass %] | 3.76 | 0.19 |
| 1,3-Butadiene [mass %] | 14.47 | 41.67 |
| Methylacetylene [mass %] | 1.03 | 0.08 |
| Vinylacetylene [mass %] | 13.80 | 0.68 |
| Ethylacetylene [mass %] | 2.77 | 0.15 |
| Others [mass %] | 0.78 | 0.18 |

TABLE 2

| | | Example 1 | Example 2 | Example 3 | Example 4 | Comparative Example 1 | Comparative Example 2 | Comparative Example 3 | Comparative Example 4 |
|---|---|---|---|---|---|---|---|---|---|
| Hydrogenation catalyst | CO adsorption amount [cm³/g] | 0.0435 | 0.009 | 0.0621 | 0.3456 | 0.0435 | 0.009 | 0.0621 | 0.3456 |
| | Specific surface area [m²/g] | 79 | 27 | 132 | 159 | 79 | 27 | 132 | 159 |
| Composition of hydrogenated product | i-Butane [mass %] | 2.43 | 2.55 | 2.53 | 3.24 | 1.99 | 2.41 | 1.89 | 2.55 |
| | n-Butane [mass %] | 3.22 | 3.11 | 5.86 | 10.36 | 7.83 | 8.72 | 9.37 | 11.89 |
| | trans-2-Butene [mass %] | 4.96 | 5.03 | 13.32 | 11.76 | 17.38 | 16.57 | 19.66 | 19.19 |
| | 1-Butene [mass %] | 14.41 | 15.09 | 13.28 | 11.82 | 33.19 | 29.57 | 25.11 | 20.97 |
| | iso-Butene [mass %] | 16.32 | 16.38 | 15.99 | 16.04 | 24.71 | 25.36 | 23.87 | 24.15 |
| | cis-2-Butene [mass %] | 33.97 | 33.86 | 32.47 | 29.75 | 7.62 | 8.51 | 9.77 | 10.18 |
| | 1,2-Butadiene [mass %] | 2.06 | 1.59 | 1.32 | 1.48 | 0.02 | 0.11 | 0.10 | 0.04 |
| | 1,3-Butadiene [mass %] | 19.53 | 19.02 | 12.32 | 11.64 | 6.52 | 8.15 | 9.35 | 10.28 |
| | Methylacetylene [mass %] | 0.25 | 0.42 | 0.17 | 0.19 | 0.04 | 0.04 | 0.09 | 0.01 |
| | Vinylacetylene [mass %] | 0.93 | 0.90 | 0.96 | 1.27 | 0.05 | 0.16 | 0.00 | 0.04 |
| | Ethylacetylene [mass %] | 0.73 | 0.62 | 0.53 | 0.78 | 0.03 | 0.06 | 0.06 | 0.03 |
| | Others [mass %] | 1.18 | 1.43 | 1.25 | 1.67 | 0.62 | 0.35 | 0.73 | 0.67 |

It can be seen from Tables 1 and 2 that in Examples 1 to 4, it is possible to efficiently hydrogenate vinylacetylene while inhibiting hydrogenation of 1,3-butadiene compared to Comparative Examples 1 to 4 in which the hydrocarbon mixture B having a vinylacetylene concentration of less than 1 mass % is used. Moreover, it can be seen from Tables 1 and 2 that in Examples 1 and 2, the concentration of 1,3-butadiene in the hydrogenated product is higher than that in the hydrocarbon mixture, and it is possible to selectively hydrogenate vinylacetylene to 1,3-butadiene and efficiently produce 1,3-butadiene.

INDUSTRIAL APPLICABILITY

According to the present disclosure, it is possible to hydrogenate vinylacetylene while inhibiting reduction of 1,3-butadiene concentration with respect to a hydrocarbon mixture containing 1,3-butadiene and vinylacetylene.

REFERENCE SIGNS LIST 10 extractive distillation section
11 evaporation column
12 first extractive distillation column
13 stripping column
14 compressor
15 second extractive distillation column
20 stripping section
21 first stripping column
22 second stripping column
30 impurity removal section
31 low boiling point substance removal column
32 high boiling point substance removal column
40 mixing section
50 hydrogenation section
60 return line
100 production apparatus

The invention claimed is:

1. A method for hydrogenating a hydrocarbon mixture containing 1,3-butadiene and vinylacetylene, the method comprising:
   providing the hydrocarbon mixture containing 1,3-butadiene and vinylacetylene,
   producing a hydrogenation catalyst through baking of an active component at 1000° C. or higher,
   contacting the hydrocarbon mixture with the hydrogenation catalyst in the presence of hydrogen to hydrogenate at least the vinylacetylene,
   wherein
   the hydrocarbon mixture contains 1 mass % or more of vinylacetylene, and
   the hydrogenation catalyst includes palladium as the active component and has a CO adsorption amount of 0.05 $cm^3/g$ or less.

2. The method according to claim 1, wherein the CO adsorption amount of 0.05 $cm^3/g$ or less is obtained after calcining the palladium having an alumina support.

3. The method according to claim 1, wherein the hydrogenation catalyst includes a support and palladium supported on the support.

4. The method according to claim 3, wherein a supported amount of the palladium is at least 0.1 mass % and not more than 5.0 mass %.

5. The method according to claim 3, wherein the support includes γ-alumina and at least one of α-alumina and θ-alumina.

6. The method according to claim 3, wherein the hydrogenation catalyst has an eggshell structure.

7. The method according to claim 3, wherein the hydrogenation catalyst has an average pore diameter of at least 5.0 nm and not more than 30 nm.

8. The method according to claim 1, wherein state the hydrocarbon mixture is in a gaseous state when the hydrocarbon mixture is brought into contact with the hydrogenation catalyst.

9. The method according to claim 1, wherein the hydrocarbon mixture includes a fraction produced in separation and recovery of 1,3-butadiene from a $C_4$ hydrocarbon mixture.

* * * * *